United States Patent [19]
Wilson et al.

[11] Patent Number: 5,935,073
[45] Date of Patent: Aug. 10, 1999

[54] EQUIPMENT AND METHOD FOR CALIBRATION AND QUALITY ASSURANCE OF AN ULTRASONIC BONE ANALYSIS APPARATUS

[75] Inventors: Kevin E. Wilson, Cambridge; Donald Barry, Norwood; Dennis G. Lamser, Arlington; John P. O'Brien, Brookline; Jay A. Stein, Framingham, all of Mass.

[73] Assignee: Hologic, Inc., Waltham, Mass.

[21] Appl. No.: 08/866,804

[22] Filed: May 30, 1997

Related U.S. Application Data

[63] Continuation-in-part of application No. 08/534,131, Sep. 26, 1995, Pat. No. 5,775,228.

[51] Int. Cl.$^6$ ............................................. A61B 8/00
[52] U.S. Cl. ............................................. 600/449
[58] Field of Search ................................. 600/437, 442, 600/438, 449; 73/1.82, 1.86

[56] References Cited

U.S. PATENT DOCUMENTS

Re. 32,782  11/1988  Pratt, Jr. .
4,361,154  11/1982  Pratt, Jr. .

(List continued on next page.)

FOREIGN PATENT DOCUMENTS 8002796  12/1980  European Pat. Off. .
0299906  1/1989   European Pat. Off. .

(List continued on next page.)

OTHER PUBLICATIONS

Connective Tissue Changes in the Menopause, M. Brincat et al.
Minhorst Osteoson brochure (May 1995).
Minhorst Osteoson K IV brochure (undated).
Ultrasound for Bone Measurement, A Private Symposium, Lunar, Apr. 1992.
Lunar, Achilles Ultrasound Bone Densitometer brochure (undated).
Clinical Investigations, "Preliminary Evaluation of a New Ultrasound Bone Densitometer" by Belinda Lees and John C. Stevenson, Calif Tissue Int. 1993.
Report on "Ultrasonic Assessment of Bone III", May 1993.
Observations at ASBMR, by G.H. Brandenburger, 1991.
"Ultrasound Measurements of the Os Calcis", by R. Mazess et al., Presented at the Third Bath Conference on Osteoporosis and Bone Mineral Measurement (Jun. 1992).
Perth International Bone Meeting, Bone Fragility in the Year 2000: Clinical Measurement, p. 63 (Feb. 1995).
Perth International Bone Meeting, Bone Fragility in the Year 2000: Clinical Measurement, p. 61 (Feb. 1995).
IGEA, DBM Sonic 1200 Brochure (undated).
"Bone" Official Journal of the International Bone and Mineral Society, vol. 16, No. 1, pp. 246–249 Jan. 1995.

(List continued on next page.)

Primary Examiner—Francis J. Jaworski
Attorney, Agent, or Firm—Cooper & Dunham LLP

[57] ABSTRACT

A method of calibrating an ultrasound bone analysis apparatus having a pair of transducer assemblies. Each transducer assembly has a transducer and a coupling pad, and is movable relative to the other so that a face of each pad can be moved to a position in which they mutually contact and to a position where the faces contact body parts. The method according to the present application includes transmitting an ultrasound signal from one transducer and receiving a signal corresponding to the transmitted ultrasound signal through the other transducer when the transducer assemblies are in the first position and the second position. A time for the ultrasound signal to pass through the body part is determined, and a width of the body part based on positions of the transducers is determined. Then, using the time and width values a speed of sound of the ultrasound signal passing through the body part with squish compensation is calculated.

4 Claims, 10 Drawing Sheets

U.S. PATENT DOCUMENTS

| | | |
|---|---|---|
| 4,421,119 | 12/1983 | Pratt, Jr. . |
| 4,774,959 | 10/1988 | Palmer et al. . |
| 4,913,157 | 4/1990 | Pratt, Jr. et al. . |
| 4,941,474 | 7/1990 | Pratt, Jr. . |
| 5,014,970 | 5/1991 | Osipov . |
| 5,025,789 | 6/1991 | Hassler . |
| 5,134,999 | 8/1992 | Osipov . |
| 5,349,959 | 9/1994 | Wiener et al. . |
| 5,452,722 | 9/1995 | Langton ................................. 600/449 |
| 5,615,681 | 4/1997 | Ohtomo ................................. 600/449 |

FOREIGN PATENT DOCUMENTS

| | | |
|---|---|---|
| 0312847 | 4/1989 | European Pat. Off. . |
| 0341969 | 11/1989 | European Pat. Off. . |
| 0516353 | 12/1992 | European Pat. Off. . |
| 0576217 | 12/1993 | European Pat. Off. . |
| 0663182 | 7/1995 | European Pat. Off. . |
| 2257253 | 1/1993 | United Kingdom . |

OTHER PUBLICATIONS

"Ultrasound Assessment of Bone Fragility in the Climacteric Women" by DBM Sonic 1200, Mura Marta.

Perth International Bone Meeting, Bone Fragility in the Year 2000, p. 65 (Feb. 1995).

"The measurement of broadband ultrasonic attenuation in cancellous bone", MEP Ltd. 1984, vol. 12 No. 2.

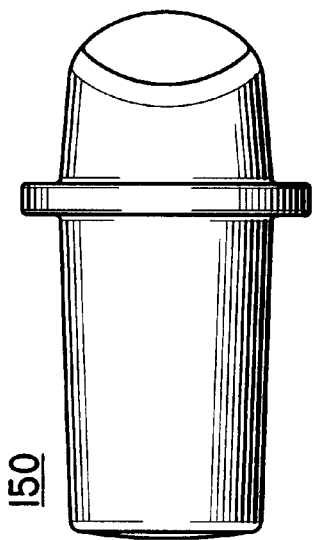
FIG. 5A
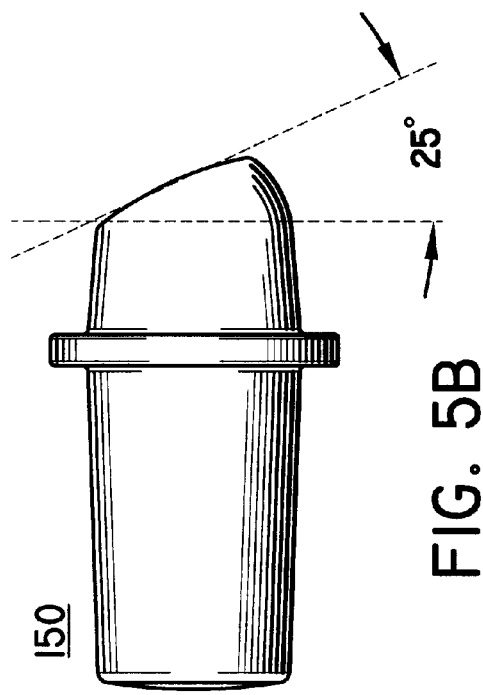
FIG. 5B
FIG. 5C

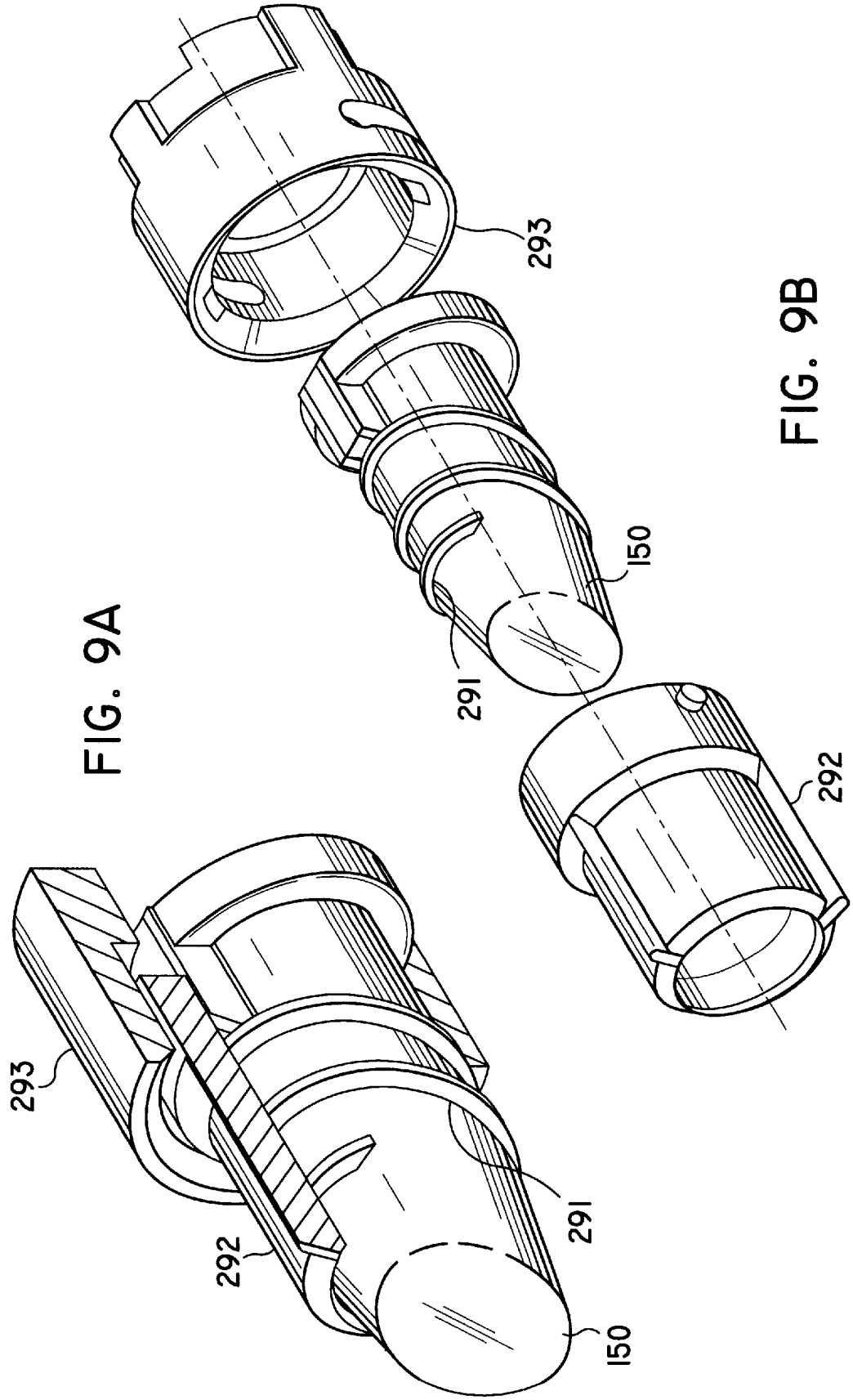

EQUIPMENT AND METHOD FOR CALIBRATION AND QUALITY ASSURANCE OF AN ULTRASONIC BONE ANALYSIS APPARATUS

CROSS REFERENCE TO RELATED APPLICATIONS

The present application is a continuation-in-part of application Ser. No. 08/534,131 filed on Sep. 26, 1995 and now U.S. Pat. No. 5,755,228, which is hereby incorporated herein by reference in its entirety.

BACKGROUND

1. Field of the Invention

This invention relates to the field of ultrasonic analysis of bone tissue in humans, and more particularly to an improvement in the calibration and quality assurance of an ultrasonic bone analysis apparatus by using, for example, phantoms.

2. Description of the Related Art

The use of ultrasound in methods for detecting changes in bone characteristics is known. In particular, an ultrasound bone analysis apparatus has been used to analyze the properties of the heel bone or os calcis. The use of ultrasound is advantageous because it is non-invasive and is well-suited to repeated measurements or studies during medication since no ionizing radiation is used.

Precision and reliability of the ultrasonic bone analysis apparatus, as with other medical diagnostic instrumentation, are a matter of substantial importance. Therefore, the apparatus undergoes calibration and quality assurance regularly during its lifetime. Rather than using a human subject, the calibration and quality assurance is performed using a substitute medium that has specific ultrasonic properties. The calibration and quality assurance facilitate adjustment of the apparatus according to the specification of the instrument.

An ultrasonic bone analysis apparatus typically measures the rate of change of attenuation of ultrasound with frequency in the range of 200 to 600 kHz ("broadband ultrasound attenuation" or "BUA"), and also the speed of passage of acoustic waves ("speed of sound" or "SOS") through the bone. The BUA is a relative quantity calculated using a baseline signal as a reference of the transmitted signal entering the bone.

The baseline is typically acquired by measuring the signal after passage through a reference medium. Because the reference signal is used to assess the transmitted signal, the reference medium should minimally affect the ultrasonic signal.

Some existing ultrasonic bone analysis systems require immersing the foot of the patient in water. Several of these same "wet systems" use water as the reference medium. While water itself generally has a minimal distortive effect on the ultrasonic signal, its use necessitates preparation and cleanup, and is inconvenient for at least these reasons.

While some commercially available phantoms are suitable for monitoring temporal changes in scanner performance, the acoustic properties of these phantoms are typically significantly different from those of bones such as the os calcis. Therefore, these phantoms might not adequately mimic the human foot.

Heretofore, Clarke et al. proposed in "A Phantom for Quantitative Ultrasound of Trabecular Bone", 39 Phys. Med. Biol. 1677–87, to use a phantom as a substitute medium in a wet system. The proposed phantom consists of a rectangular block manufactured from a mixture of liquid epoxy and gelatine particles. While the proposed phantom does have acoustic properties similar to bone and may be adequate for experimental purposes, Clarke et al. admit that the proposed phantom has a number of unsolved practical problems such as durability.

A phantom manufactured from an epoxy and glass bead mixture has also been used with a wet system. However, the manufacture of this phantom is believed to be complex and to require substantial supervision and control.

The measurement of SOS depends on the ambient conditions. Measuring accurately and comparing SOS data can be difficult due to the wide range of possible conditions, and such difficulties can be aggravated by imprecise control and determination of the conditions of the measurement.

Various media have been used for testing SOS measurements. Pure water and saline solution of various sodium chloride concentrations have been employed. However, the SOS for each of these substances varies according to temperature, each substance having a positive temperature coefficient. Therefore, using one of these substances in the testing of the SOS measurements has the disadvantage that temperature is an additional variable.

While ethyl alcohol is known to have a negative temperature coefficient of sound propagation, mixing ethyl alcohol with water tends to cancel the positive temperature coefficient of sound propagation in the water. A mixture of 17% ethyl alcohol by weight has a substantially zero temperature coefficient of sound propagation over a large range of temperatures.

SUMMARY

The present application provides a method of calibrating an ultrasound bone analysis apparatus. The apparatus includes at least a pair of transducer assemblies which are movable relative to each other. Each transducer assembly has a transducer and a coupling pad. In one embodiment, the method includes providing a pair of ultrasound transducer assemblies that are movable between a first position where a face of each coupling pad are in contact and a second position where the face of each coupling pad are coupled to a body part. An ultrasound signal is transmitted through one coupling pad and a signal corresponding to the transmitted ultrasound signal is received through another coupling pad when the transducer assemblies are in the first position and the second position. A time for the ultrasound signal to pass through the body part and a width of the body part based on positions of the transducers are then determined. Using the time and width values a speed of sound of the ultrasound signal passing through the body part with squish compensation is calculated.

BRIEF DESCRIPTION OF THE DRAWINGS

Preferred embodiments of the invention are described hereinbelow with reference to the drawings wherein:

FIGS. 5A and 5B are front and side views of a pad/delay unit of the ultrasonic bone analysis apparatus;

FIG. 5C is a contour diagram of an end of the pad/delay unit;

FIGS. 9A and 9B are a perspective view and an exploded view, respectively, of a transducer assembly of the ultrasonic bone analysis apparatus.

DETAILED DESCRIPTION

Ultrasonic Bone Analysis Apparatus

Figure 1:
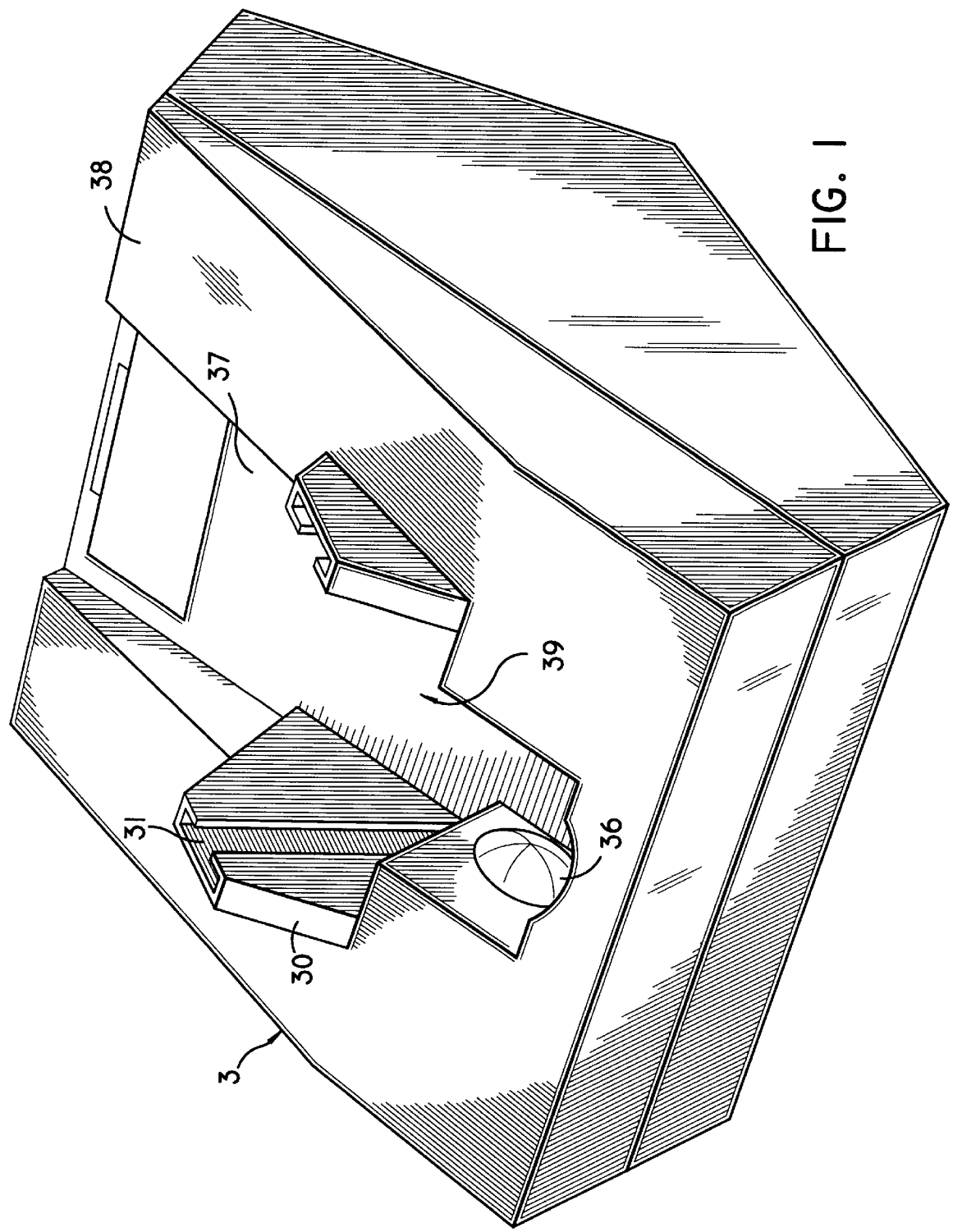
FIG. 1 is a perspective view of a foot well assembly of an ultrasonic bone analysis apparatus that can use phantoms according to the present application.

Referring to FIG. 1, an ultrasonic bone analysis apparatus with which the phantoms according to the present application can be used has a foot well assembly 3. The foot well assembly 3 includes a box cover 38 having a foot support 39, and foot well bottom 37. The foot support 39 has an area slightly larger than a human foot. Transducer ports 36 are located on the sides of the foot support 39, towards the rear. Bridge brackets 30 with respective channels 31 which are located along the sides of the foot support 39 facilitate the mounting of a shin guide assembly (not shown) for restraining the foot and lower leg.

Figure 2:
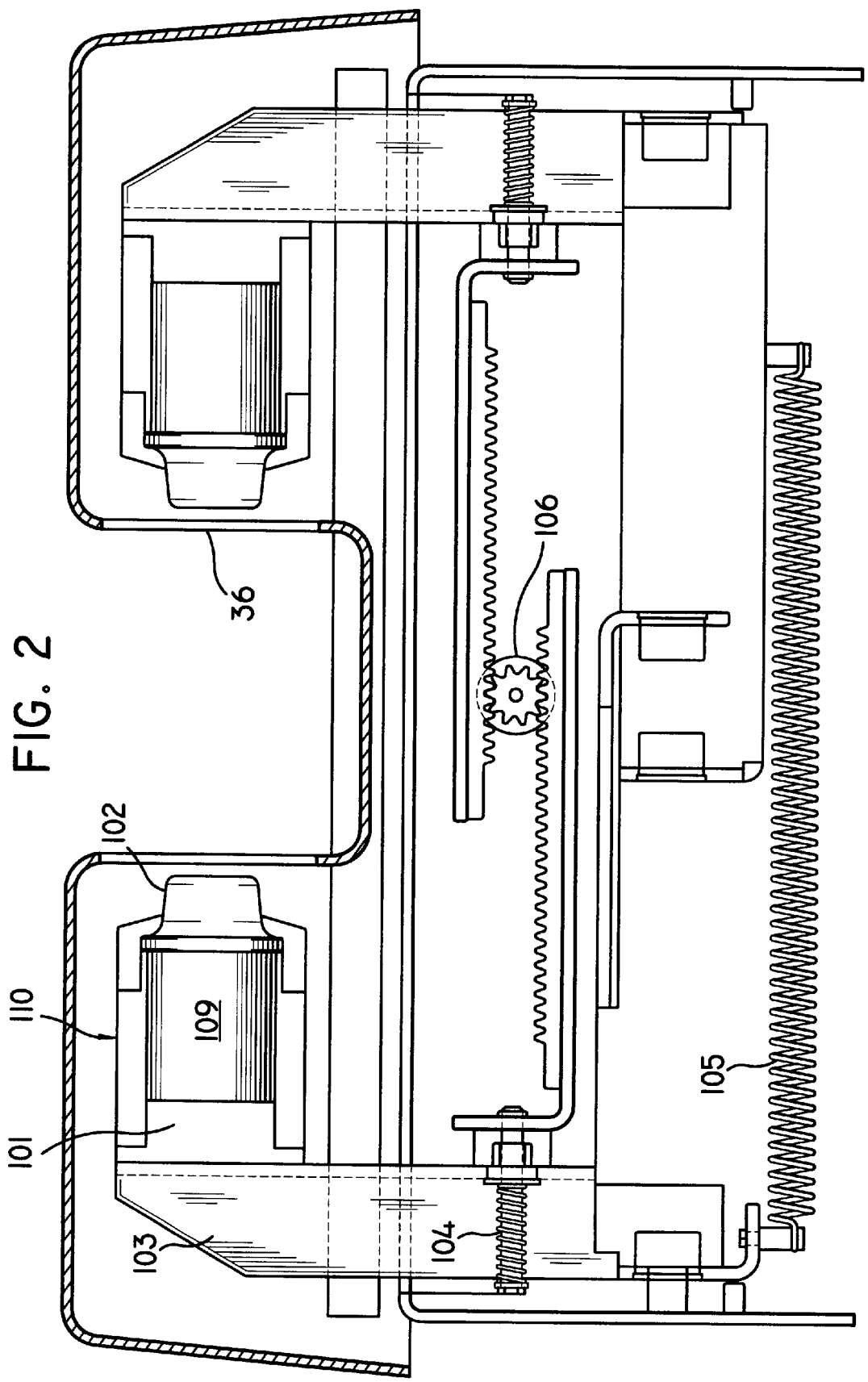
FIG. 2 is a sectional view of a transducer drive mechanism of the ultrasonic bone analysis apparatus.

Referring now to FIG. 2, a transducer drive mechanism of the ultrasonic bone analysis apparatus includes a pair of transducer assemblies 110. The transducer assemblies 110 include respective transducers 101, respective acoustical delay lines 109 and respective coupling pads 102.

The transducer assemblies 110 are mounted to respective carriages 103 that slide along a lateral-medial axis. The carriages 103 are provided with sufficient freedom of movement such that the respective coupling pads 102 can be brought into mutual contact. Respective compression springs 104 attached to the carriages 103 apply opposing lateral forces towards the center of the foot or phantom. The carriage/spring assembly is free floating and will center itself on the foot or phantom with equal pressure on both sides.

An extension spring 105 applies the initial pressure when the coupling pads 102 reach the phantom or the patient's foot. To adjust the pressure in small increments, a stepper motor with rack and pinion mechanism 106 will move a finite number of steps and compress the compression springs 104 that are attached to the respective carriages 103. The compression springs 104 will pull the respective transducers 101 and pads 102 inward at a force proportional to the spring rate and distance translated.

Figure 3:
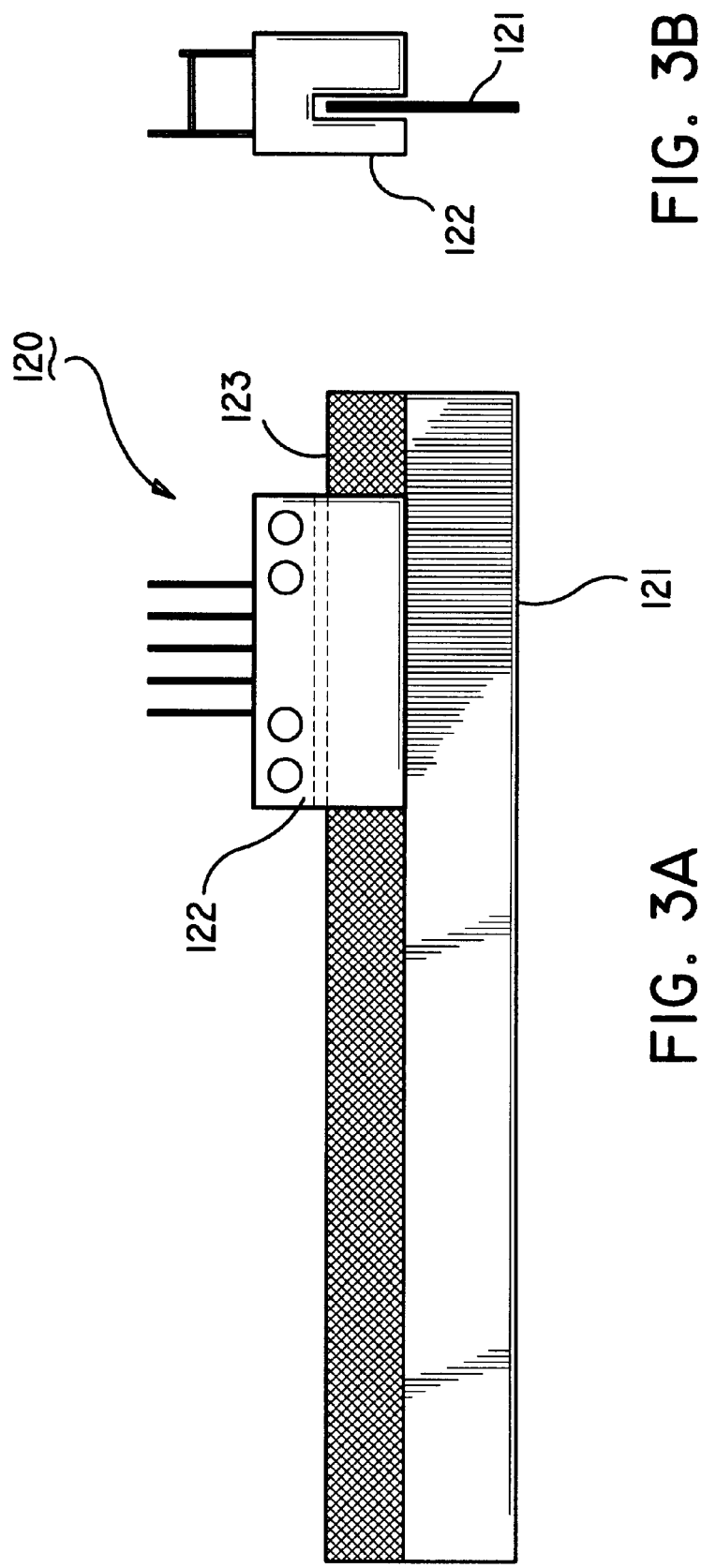
FIGS. 3A and 3B are front and side views of a position encoder of the ultrasonic bone analysis apparatus.

The distance between the transducers 101 is continuously measured by means of a position encoder 120 that is mechanically linked to the motion of the transducers 101. FIGS. 3A and 3B illustrate respective front and side views of the position encoder 120. The position encoder has a code strip 121 mounted onto one of the carriages 103 and an optical encoder reader 122 mounted on the other of the carriages 103. As the distance between the transducers 101 changes, the code strip 121 moves between the slot of the optical encoder reader 122, and the optical reader 122 reads lines 123 of the code strip 121 as the lines 123 are traversed.

Figure 4:
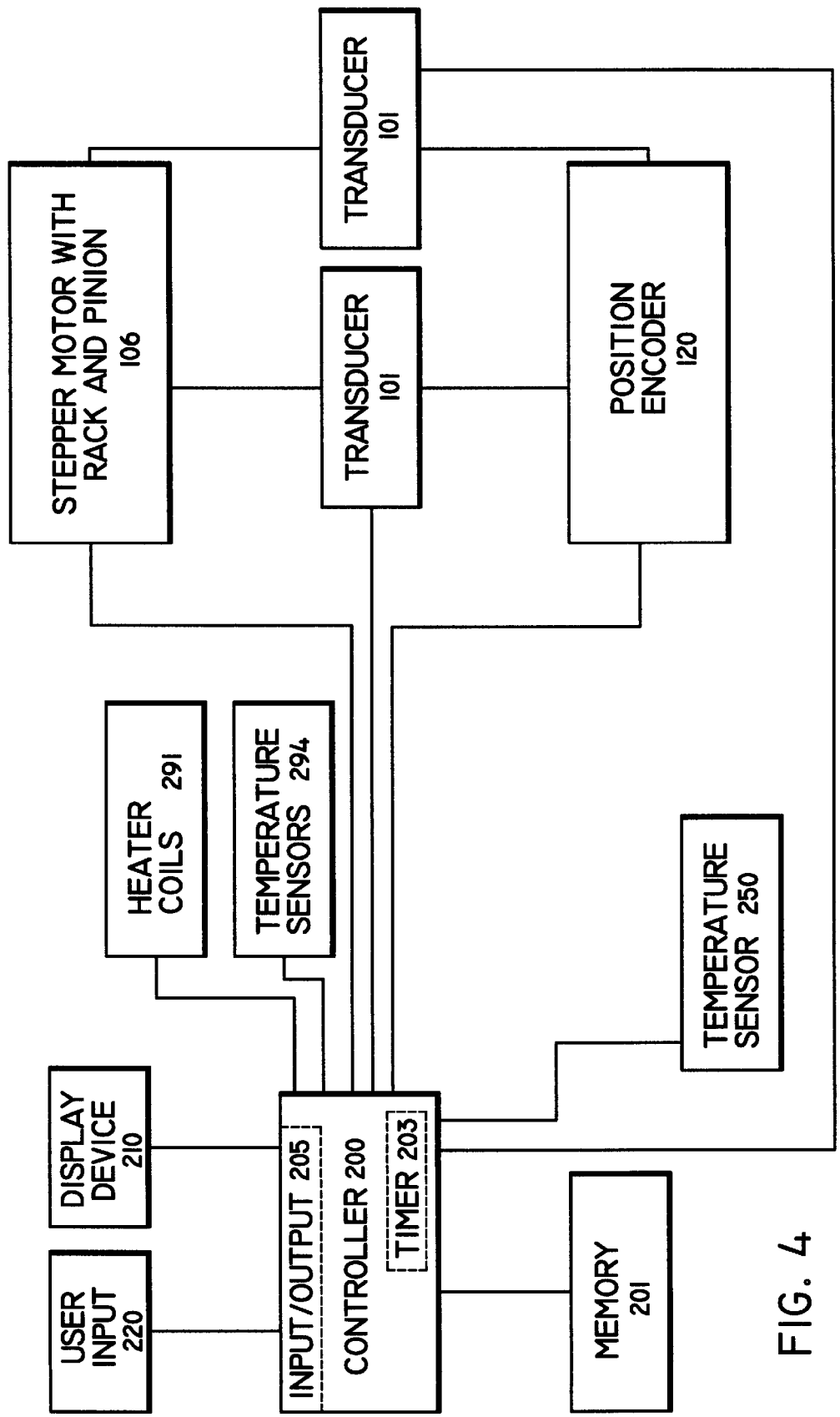
FIG. 4 is a block diagram showing control of the transducer drive mechanism of the ultrasonic bone analysis apparatus.

Referring to FIG. 4, the stepper motor with rack and pinion mechanism 106 under the control of controller 200 automatically positions transducers 101 against the patient's heel or the phantom with sufficient pressure to insure ultrasonic coupling. Signals received by the receiving transducer 101 are supplied to the controller 200. The microprocessor-based controller 200 controls the execution of system and application software and has a timer 203 and input/output circuitry 205 for interfacing with user input 220 and display device 210. Data and the system and application software are stored in memory 201 (e.g., RAM and ROM).

Preferably, the controller 200 controls the operations of the stepper motor 106 according to positional data supplied by the position encoder 120. The controller 200 monitors the position encoder 120 throughout the measurement to detect movement of the transducers 101 which may have a deleterious effect on the measurement.

Alternatively, the controller 200 determines the quality of the signals received by the receiving transducer 101 at least in part according to the attenuation of the signals, and controls the operations of the stepper motor 106 according to the quality of the signals received by the receiving transducer 101 and positional data supplied by the position encoder 120. These steps are repeated by the controller 200 until the signals received by the receiving transducer 101 achieve a predetermined quality.

The controller 200 determines other parameters of interest, including BUA and bone velocity. Also, the controller 200 uses timing data supplied by the timer 203 to determine the arrival time of the received ultrasonic signal combined with timing data for the reference signal which is stored in memory and the distance between the transducers as determined by the position encoder 120 to calculate the speed of the ultrasonic signals through the foot or phantom (or the SOS).

The controller 200 uses temperature readings from temperature sensor 250 to improve the accuracy of the position encoder measurements and correct for temperature dependent inaccuracy in the ultrasound measurement. For example, the controller 200 accounts for linear expansion of the encoder strip 121 by applying a temperature dependent term to the data supplied by the position encoder 120. Additionally, the controller 200 applies a temperature dependent term to correct an estimation of the time delay through the delay line 109 and the coupling pad 102. The controller 200 also applies a temperature dependent term to correct an estimation of the frequency-dependent attenuation of the coupling pad 102. Furthermore, the controller 200 uses the temperature reading to determine if the apparatus is operating within the specified environmental range allowed, and if not, the operator is informed that the apparatus is not ready to be used.

The coupling pads 102 have a durometer corresponding to a sufficiently flexible waveguide that can partially conform to the shape of a foot. The shape of the pads 102 conforms to the heel to eliminate any gaps between the foot and pad. The surfaces of the pads 102 which contact the transducers 101, the delay line 109, or the patent's skin is shaped at an angle to the propagation axis to reduce the acoustic reflection at the pad-to-skin interface by spreading the reflected energy over time and position.

The coupling pad 102 and the delay line 109 are integrated into a single pad/delay unit 150 to reduce an extraneous reflection between a pad-to-delay-line interface. FIGS. 5A and 5B illustrate top and side views of the pad/delay unit 150. The surface of the pad that contacts the patient's skin is shaped to expel air bubbles from the contact area when pressure is applied. FIG. 5C shows the contours of the surface of the pad/delay unit 150 which contacts the patient's skin.

A First Phantom

When executing software for calibration or quality assurance, the controller 200 via the display device 210 prompts the operator to insert a phantom in the foot support 39 of the foot well assembly 3.

Figure 6B:
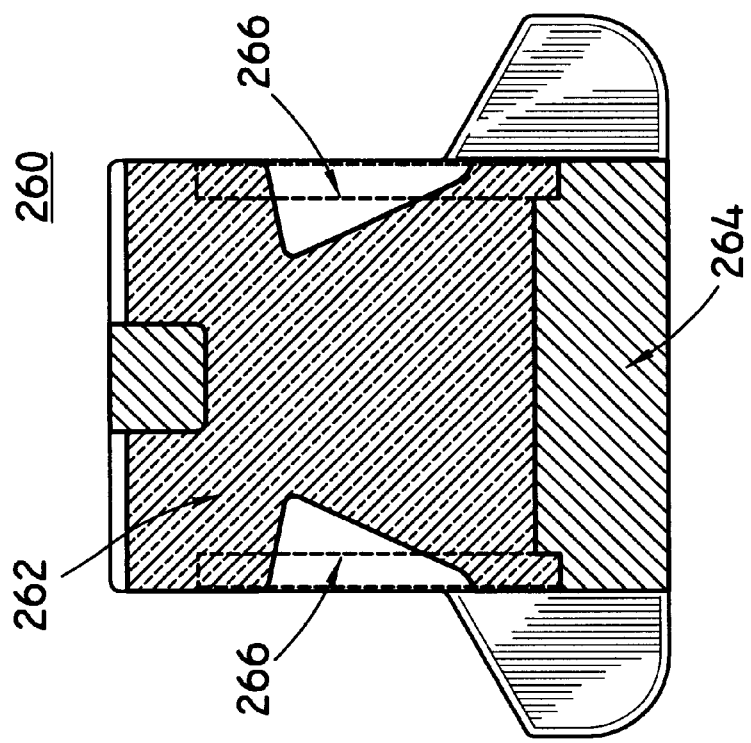
FIG. 6B is a sectional view of the first phantom taken essentially on the line 6B—6B of FIG. 6A.
Figure 6A:
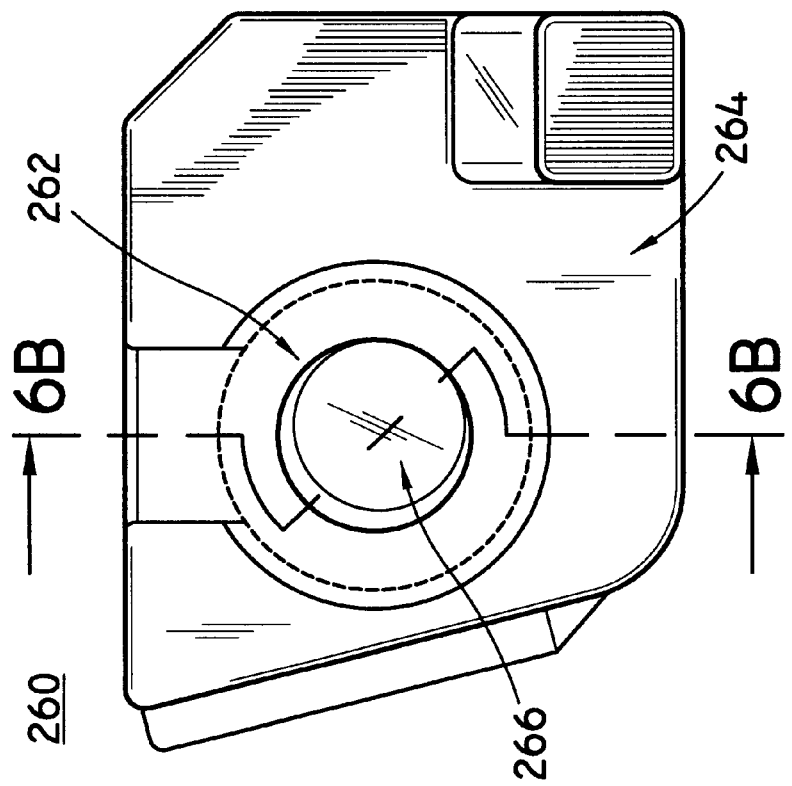
FIG. 6A is a front view of a first phantom according to the present invention.

FIGS. 6A and 6B illustrate a phantom 260 having a cylindrical plug 262 cast inside a hard plastic housing 264. The cylindrical plug 262 is a soft elastic material having a very low attenuation coefficient. The sound impedance of the soft elastic material is relatively close to that of soft human tissue. The attenuation-versus-frequency profile of the material in the frequency range of 200–1000 kHz is substantially flat. The soft elastic material has a minimal effect on the ultrasonic wave, and a predetermined SOS.

The soft material is preferably an elastomeric, white castable polyurethane set to a durometer of 10 to 50 Shore A. One such material is Ciba-Geigy TDT 178-34, which has a durometer of 15 Shore A and is also the preferred material of the transducer pads 150.

Indentations 266 are provided on opposite sides of the cylindrical plug 262 to accommodate the respective transducer pads 150. The shapes of the indentations 266 complement the shapes of the respective transducer pads 150. The hard plastic housing 264 positions the cylindrical plug 262 properly in relation to the transducer pads 150 of the apparatus. The complementary shapes of the pads 150 and respective indentations 266 of the cylindrical plug 262 facilitate the coupling of the pads 150 with the plug 262.

The phantom 260 has approximately the width of the typical female heel, and thereby mimics the conditions at which the heel is measured. As a result, the reference signal spreads out in a pattern similar to that in an ultrasonic measurement of the heel.

When the phantom 260 is inserted in the apparatus, a signal is transmitted through the phantom. The controller 200 controls movement of the transducer assemblies 110 using feedback from the encoder 120. The received signal which had passed through the phantom 260 is used to calibrate the apparatus. Using timing data supplied by the timer 203, the controller 200 calculates the propagation time of the transmitted signal through the phantom 260. The controller 200 saves data of the received signal in the memory 201 and uses the saved data in subsequent calculations of BUA and SOS. The propagation time through the phantom 260 is used to calibrate a zero point of the apparatus, so that the propagation time through the foot can be calculated at a later time. The zero point is the difference between a predetermined time of propagation through the phantom 260, including an adjustment for temperature, and the measured time of propagation of a transmitted ultrasound signal through the phantom 260.

The controller 200 also determines the frequency spectrum of the received signal which is used in the BUA calculation. The received signal that passed through the phantom 260 is used as a baseline with which a signal that passes through the foot is compared. The BUA calculation will be explained in more detail hereinbelow.

The phantom 260 is also used for quality assurance of the apparatus. In this mode, the controller 200 calculates the drift of the apparatus by using the measurement of the current received signal that passed through the phantom 260 and recorded measurements of past received signals that had passed through the phantom 260 which are stored in memory 201. The drift is temperature-dependent. Therefore, because the human foot is typically at 98.6 degrees F. and the phantom 260 is at room temperature (generally between 60–90 degrees F.), the measured value is temperature-corrected according to the temperature reading from the temperature sensor 250.

A Second Phantom

Figure 7A:
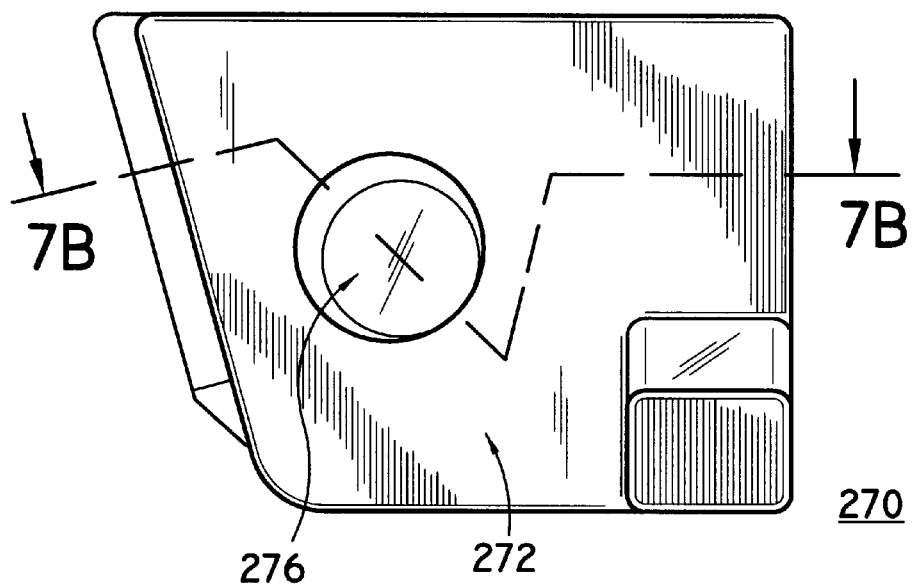
FIG. 7A is a front view of a second phantom according to the present invention.
Figure 7B:
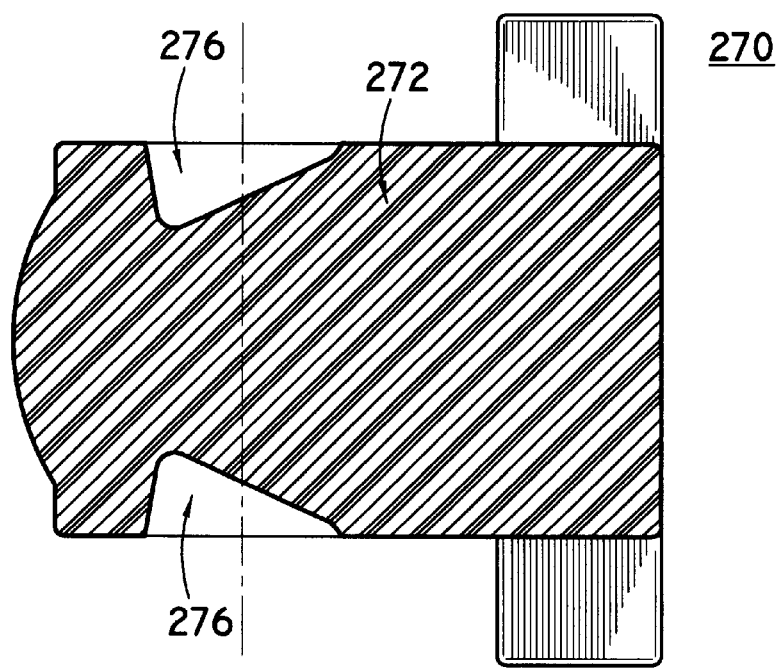
FIG. 7B is a sectional view of the second phantom taken essentially on the line 7B—7B of FIG. 7A.

Referring to FIGS. 7A and 7B, a phantom 270 is provided to mimic the BUA of the human foot. The phantom 270 attenuates an ultrasonic wave in the frequency range of 200–1000 kHz by approximately the same amount as a human foot. The attenuation-versus-frequency profile of the phantom 270 is substantially linear in the frequency range of 200–600 kHz and is approximately 1 dB/MHz per mm. This profile is very similar to the attenuation-versus-frequency profile of the human foot.

The phantom 270 is a cut, castable, or otherwise manufactured block of material 272 having indentations 276 on opposite sides thereof to accommodate the respective transducer pads 150. The shapes of the indentations 276 complement the shapes of the respective transducer pads 150. The complementary shapes of the pads 150 and respective indentations 276 facilitate the coupling of the pads 150 with the block 272.

The phantom 270 also has approximately the width of the typical female heel, and thereby mimics the conditions at which the heel is measured. The block 272 is shaped to position the phantom 270 properly in relation to the transducer pads 150 when the phantom 270 is placed in the foot support 39 of the apparatus.

The block 272 is preferably a castable polyurethane. One such polyurethane is black and has approximately an 80 Shore A durometer. The polyurethane block is simple to manufacture and suitably mimics the human foot.

Software for calibration and quality assurance also measures a received signal that passed through the phantom 270. The steps for acquiring this measurement are similar to the steps for acquiring a measurement of the signal that passed through the phantom 260, as set forth hereinabove.

The received signals that passed through the phantom 270 are used for quality assurance of the apparatus for a BUA measurement. The BUA of a measured signal is calculated in the frequency domain. The measured signal and the reference signal in the time domain are transferred to respective frequency-domain counterparts $|B(f)|$ and $|R(f)|$ by performing a Fourier Transform or a Fourier Series calculation. The BUA is the slope of a line fit to a function $A(f)$ in a specific frequency range. The function $A(f)$ is defined as follows:

$$A(f=20*\log_{10}(|B(f)|/|R(f)|).$$

A commonly used frequency range is 0.2 to 0.6 MHz.

As mentioned hereinabove, the reference signal may be obtained by measuring a signal that passed through the phantom 260. Magnitudes of respective frequency components of this reference signal are used as the reference $|R(f)|$.

The same reference signal may be used as the reference for calculating the BUA of a signal that passed through the phantom 270. In such a calculation, the magnitudes of the respective frequency components of the signal that passed through the phantom 270 are the $|B(f)|$ of the measured signal.

The measurement of the received signal that passed through the phantom 270 is used by the quality assurance software to determine instrument drift. Because the phantom 270 mimics the human foot, the determined drift would reflect the expected drift when a human foot is analyzed using the apparatus. Again, because drift is temperature-dependent, the calculation includes a temperature correction term.

A Third Phantom

Figure 8A:
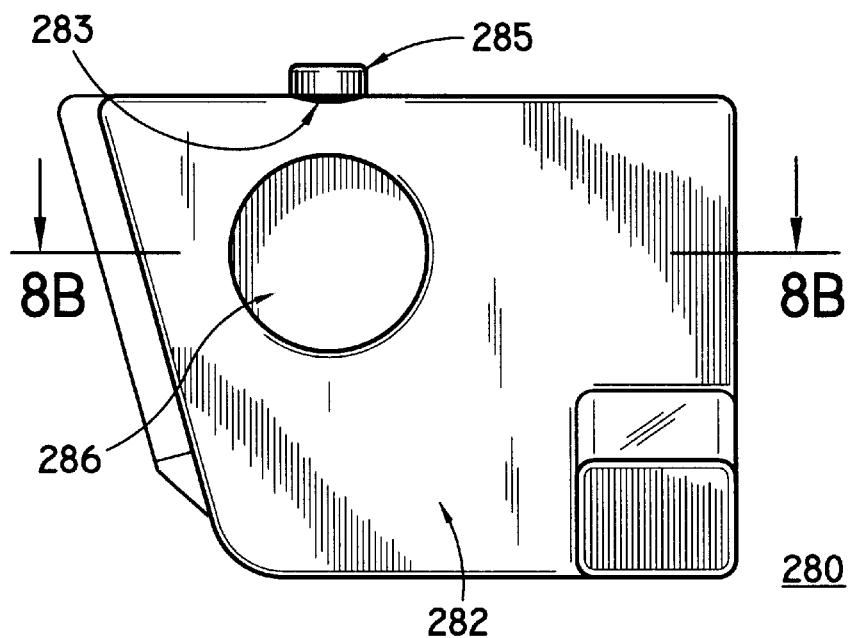
FIG. 8A is a front view of a third phantom according to the present invention.
Figure 8B:
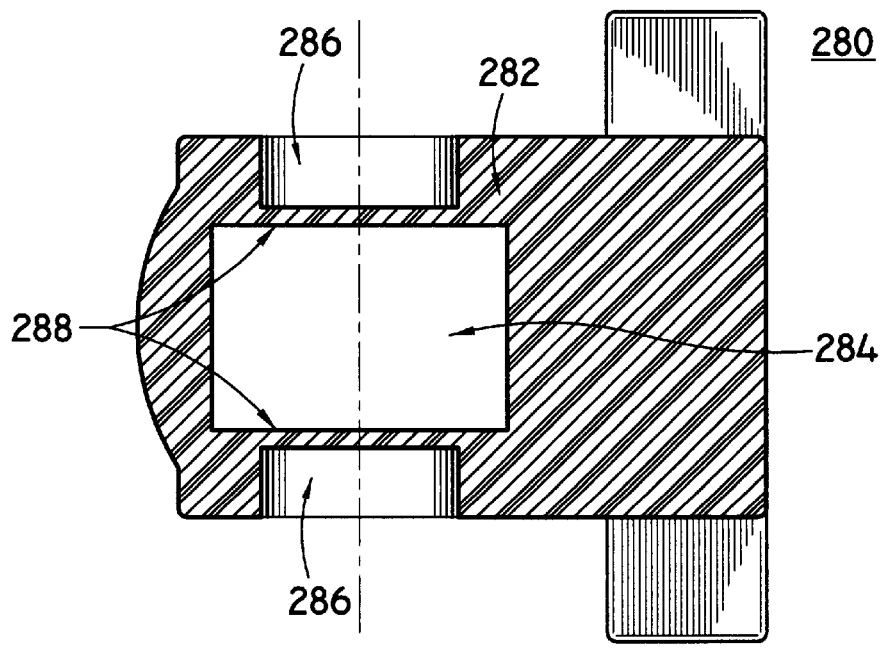
FIG. 8B is a sectional view of the third phantom taken essentially on the line 8B—8B of FIG. 9A.

FIGS. 8A and 8B illustrate a phantom 280 that has a substantially zero temperature coefficient over a range of normal ambient temperatures.

The temperature-independent phantom 280 has a housing 282 containing a mixture of ethyl alcohol and water which is 17% ethyl alcohol by weight. The housing 282 has a filler port 283 through which the mixture is introduced. A cap 285 plugs the filler port 283 after the mixture fills a receptacle 284 formed by inner walls of the housing 282. The plugged receptacle 284 is air-tight to prevent a change in alcohol concentration by evaporation of the alcohol or absorption of water by the mixture. The housing 282 is made from preferably a polymer such as polyurethane which has a predetermined SOS.

Indentations 286 are provided on opposite sides of the housing 282 to accommodate the respective transducer pads 150. The bottoms of the respective indentations 286 are parallel to respective adjacent inner walls 288 of the housing. Therefore, the shapes of the indentations 286 do not complement the shape of the respective transducer pads 150. Nevertheless, because the pads 150 are elastomers, when the phantom is placed in the foot support 39, the transducer assemblies 110 can be moved under the control of controller 200 to compress the respective transducer pads 150 against the bottoms of the respective indentations 286 until there is adequate coupling. The compression of the transducer pads 150 does not affect the SOS measurement.

The housing 282 between each of the indentations 286 and the mixture should be relatively thin compared to the distance between the inner walls 288. The other portions of the housing 282 can be relatively thicker than the distance between the indentations 286 and the respective adjacent inner walls 288.

The phantom 280 also has approximately the width of the typical female heel, and thereby mimics the conditions at which the heel is measured. The housing 282 is shaped to position the phantom 280 properly in relation to the transducer pads 150 when the phantom 280 is placed in the foot support 39 of the apparatus.

Because the housing 282 encloses the fluid mixture, the phantom 280 is convenient to use. Furthermore, the phantom 280 having a polymer housing is easily manufactured.

The phantom 280 is used to calibrate the apparatus for the SOS calculation. Furthermore, the phantom 280 can be used for quality assurance to measure instrument drift. Because the phantom 280 has a predetermined SOS that is temperature-independent, the drift can be determined by comparing the measured value with the predetermined value. The steps for acquiring a signal that passed through the phantom 280 are similar to the steps for acquiring a signal that passed through the phantom 260, as set forth hereinabove.

The phantom 280 as described is substantially temperature-independent over a range of normal ambient temperatures because a mixture of ethyl alcohol and water which is 17% ethyl alcohol by weight is used. The temperature independence is preferred. Alternatively, the 17% mixture can be replaced by pure water or a mixture of water and ethyl alcohol which has a predetermined temperature coefficient. Measurements of an ultrasonic signal that passed through a phantom using pure water or the alternative mixture would need to be adjusted with an appropriate temperature-correction term which can be determined by one skilled in the art.

Mutualy Contacting Transducer Pads

A reference signal can be obtained by another method using the ultrasonic bone analysis apparatus without a phantom. The controller 200 controls movement of the transducer assemblies 110 until the transducer pads 150 are mutually in contact. A received signal that passed through the mutually touching transducer pads can be used for many of the same purposes, which are described hereinabove, for which the received signals that passed through the phantom 260 is used.

It is desirable to obtain calibration measurements that account for variations in ultrasonic and electronic properties according to respective variation in temperature and time. The measurement of the received signal that passed through the mutually contacting coupling pads is obtained relatively close in time to a measurement of a signal passing through a heel or a phantom interposed between the pads. Because proximity in time is accompanied, presumptively, by proximity in ambient temperatures for the respective measurements, no correction for time or temperature drift between the measurements is required. Therefore, the measured signal obtained while the pads 150 are mutually touching may be used to compare with the signal that passed through the heel to measure quantities that are of interest to bone quality without contamination of the measurement by the ambient temperature at which the measurement was taken.

The received signal that passed through the mutually touching pads may be used as a reference for a BUA measurement. Additionally, a propagation time of the ultrasonic signal through the mutually touching pads is measured and may be used as a reference time for propagation through the pads. The reference time measurement may be compared to the measurement of the signal that passed through the heel to determine a time of propagation through the heel. The calculated time of propagation through the heel along with information about the width of the heel are used to calculate a SOS of the heel.

The received signal that passed through the mutually touching pads may be compared to an ultrasonic signal measured at a known temperature, and the time of arrival of the two may be used to calculate an effective temperature of the pads. The effective temperature may be used to adjust temperature-dependent coefficients of the BUA for the temporally-proximate measurements of the signals that pass through the heel or phantom.

The transmission of an ultrasonic signal through mutually contacting coupling pads may produce a reflected signal from a reflection by either the interface between the pads, a reflecting object placed in the pads, or a non-transmitting transducer face. A measurement of the reflected signal may be used to determine a time of propagation through all or part of the transmitting media, including the transducer 101 and the transducer pads 150, and scaled for comparison to the temporally-proximate measurement of the signal passing through the heel or phantom.

Transmission of an ultrasonic signal through non-contacting coupling pads can also produce a reflected signal. A measurement of the reflected signal produced from a reflection by either the interface between the pad and air, a reflecting object placed in the pads, or an object interposed between the pads may be used for the same purposes as the measurement of the reflected signal produced by transmitting through mutually contacting coupling pads.

SOS Measurements

Measurements of the speed at which ultrasound signals pass through bone (SOS) and broadband ultrasound attenuation (BUA) involve various considerations. An important consideration in obtaining accurate determinations of the SOS is pad squish (i.e., the distance a pad is compressed when pressure is applied to it).

As noted, the SOS of a body part (e.g., the heel) is a function of the width "w" of the body part and the time "t" it takes the ultrasound to pass through the heel. The SOS of a body part is represented by the following expression:

$$SOS = w/t$$

As an illustration with a typical heel being about 33 mm wide, if the coupling pads squish by 1 mm, the SOS determination may differ from an SOS determination with squish compensation by about 1/33 which is a 3.3% difference. A more desirable difference in SOS measurements is below 1% and is preferably about 0.3%.

Pad squish is dependent on various factors including pad stiffness, ambient temperatures and the age of the pad. For example, when the pads are pressed against the heel, stiff or rigid pads will have less squish as compared to pads which are more pliable. Further, the ambient temperature and age of the pad may affect the pliability of the pads. As a result, the width w and time t determinations may vary from measurement to measurement.

The speed of sound value with squish compensation (SOS') is represented by the following expression:

$$SOS' = w'/t'$$

The width w' is not the same as the width w of the body part (e.g., patient's heel), because the width w' includes the amount of squish when the coupling pads are touching and when the pads are pressed against the heel. The relationship between w' and w can be expressed as follows:

$$w' = w(1+\delta)$$

where $\delta$ is the difference between the amount of squish when the pads touch and when the pads contact the body part divided by the width w of the body part. Generally $\delta \ll 1$. Further, the time t' is not the same as time t because the ultrasound signal may travel a greater or lesser distance depending upon the amount of pad squish between the two measurements. The relationship between t' and t can be expressed as follows:

$$t = t(1+\epsilon), \text{ where } \epsilon = ((w)(\delta)/SOS_{pads})/t$$

In the expression for $\epsilon$, the numerator is the difference in squish of the two measurements divided by the SOS of the coupling pad material. This accounts for the time it takes the ultrasound to travel through the pads because of the greater or lesser squish of the coupling pads that occurs in the two measurements. Generally, the numerator is significantly smaller than the dominator because the time t it takes the ultrasound signal to pass through the body part is significantly greater than the time it takes the ultrasound signal to pass through the difference in pad squish.

As noted above, in order to obtain more accurate SOS values the relationship between the actual SOS and approximated SOS' determinations should be as close as possible. The relationship between the SOS and SOS' can be derived as follows. Substituting the theoretical values for w' and t', SOS' can be expressed as:

$$SOS' = (w/t)(1+\delta)/(1+\epsilon)$$

Since $\epsilon$ is substantially smaller than one, the above equation can be expanded as a power series which results in the following expression with SOS substituted for w/t:

$$SOS' = SOS(1+\delta)(1-\epsilon+o^2(\epsilon))$$
$$= SOS(1+\delta-\epsilon+o^2(\epsilon))$$

This expression can be further reduced by rewriting $\epsilon$ in terms of $\delta$:

$$SOS' = SOS(1-((w)(\delta)/SOS_{pads})/t+\delta+o^2(\delta))$$
$$= SOS(1+\delta(1-SOS/SOS_{pads})+o^2(\delta))$$

Using this expression, a determination of how closely the speed of sound with squish compensation SOS' tracks the SOS can be made. For this determination only the first term is needed because it is the largest and because $\delta$ is very small, as noted above. Referring to the above illustration where a typical heel is about 33 mm wide and the total squish of the pads is about 1 mm, and that the difference between the squish when the pads touch and when the pads contact the body is about 0.5 mm, then $\delta$ would equal about 0.5/33 or 0.015, if the coupling pads are made of a material having a value for $SOS_{pads}$ pads which is in the approximate middle of the biological range of between about 1450 m/s and about 1670 m/s (e.g., 1560 m/s). As an example, if the patient was at 1450 m/s then $1-SOS/SOS_{pads}$ would be about 0.076. As a result, SOS' will differ from SOS by about 0.11% (0.015×0.076 =0.0011 or 0.11%). Thus, the difference between SOS' and SOS is dependent on the $\delta(1-SOS/SOS_{pads})$ term of the above expression.

As discussed above, the preferred way to determine the time t' and the width w' includes transmitting an ultrasound signal from one pad to the other when the pads are touching and measuring a first propagation time $t_1$ for the ultrasound signal to pass from one pad to the other. At the same time, the position encoder determines a first position $ep_1$ of the pads. A patient's body part, e.g., the heel, is then positioned between the coupling pads and an ultrasound signal is again transmitted between the pads. The ultrasound signal is measured and a second propagation time $t_2$ is determined. At the same time, the position encoder determines a second position $ep_2$ of the pads. The difference in propagation time measurements, i.e., $t_2-t_1$, is used to determine the time t' it takes the ultrasound to pass through the patient's body. The difference in encoder positions, i.e., $ep_2-ep_1$, is used to determine the width w' of the patient's body part. As discussed above, the encoder has a code strip mounted onto one transducer assembly and an optical encoder reader mounted on the other transducer assembly. The code strip moves in a slot in the optical encoder reader, and the optical reader reads lines of the code strip as the lines are traversed. Preferably, the number of lines traversed are converted to meters.

By using the encoder to measure the width w' of the body part, the determination of SOS' is self-adjusting because if the durometer of the pads change with age or temperature they will squish to a greater or lesser extent on both measurements so the difference will not substantially change.

An alternative technique for measuring SOS' according to the present application includes transmitting an ultrasound signal when the pads are touching and determining a propagation time $t_3$ for the ultrasound signal to pass through the pads. At the same time, a position of each transducer is determined and recorded as $P_1$ and $p_2$. A patient's body part, e.g., the heel, is then positioned between the coupling pads and an ultrasound signal is again transmitted between the pads. The ultrasound signal is measured and a propagation time $t_4$ for the ultrasound signal to pass through the pads and body part is determined. At the same time, the position of each transducer is again determined and recorded as $p_3$ and $p_4$. The position $p_1$ and $p_3$ relate to one transducer and positions $p_2$ and $p_4$ relate to the other transducer. The difference in propagation time measurements (i.e., $t_4$–$t_3$) is used to determine the time t' it takes the ultrasound signal to pass through the body part.

The width w' of the body part with squish compensation is determined by determining a distance between positions $p_1$ and $p_3$ of the transducers and calculating a first width $w_1$, and then determining a distance between positions $p_2$ and $p_4$ of the transducers and calculating a second width $w_2$. The difference of the widths $w_1$, and $w_2$ is the width w' of the body part with squish compensation.

Other Provisions Related to Temperature

The present invention makes other provisions for controlling the environment of the transmission media.

Referring to FIGS. 9A and 9B, the transducer assembly 110 includes a heater coil 291, a cap 292, and a housing 293. The heater coil 291 is wrapped around a portion of the coupling pad 150. The cap 292 isolates the heater coil 291 from the housing 293. Furthermore, a temperature sensor 294 (shown in FIG. 4) is buried inside the coupling pad 150, and thereby the temperature of the pad 150 can be monitored. The controller 200 monitors a temperature reading supplied by the temperature sensor 294 and controls the heater coil 291 accordingly to maintain the pads 150 at a predetermined temperature, such as approximately body temperature.

Figure 10:
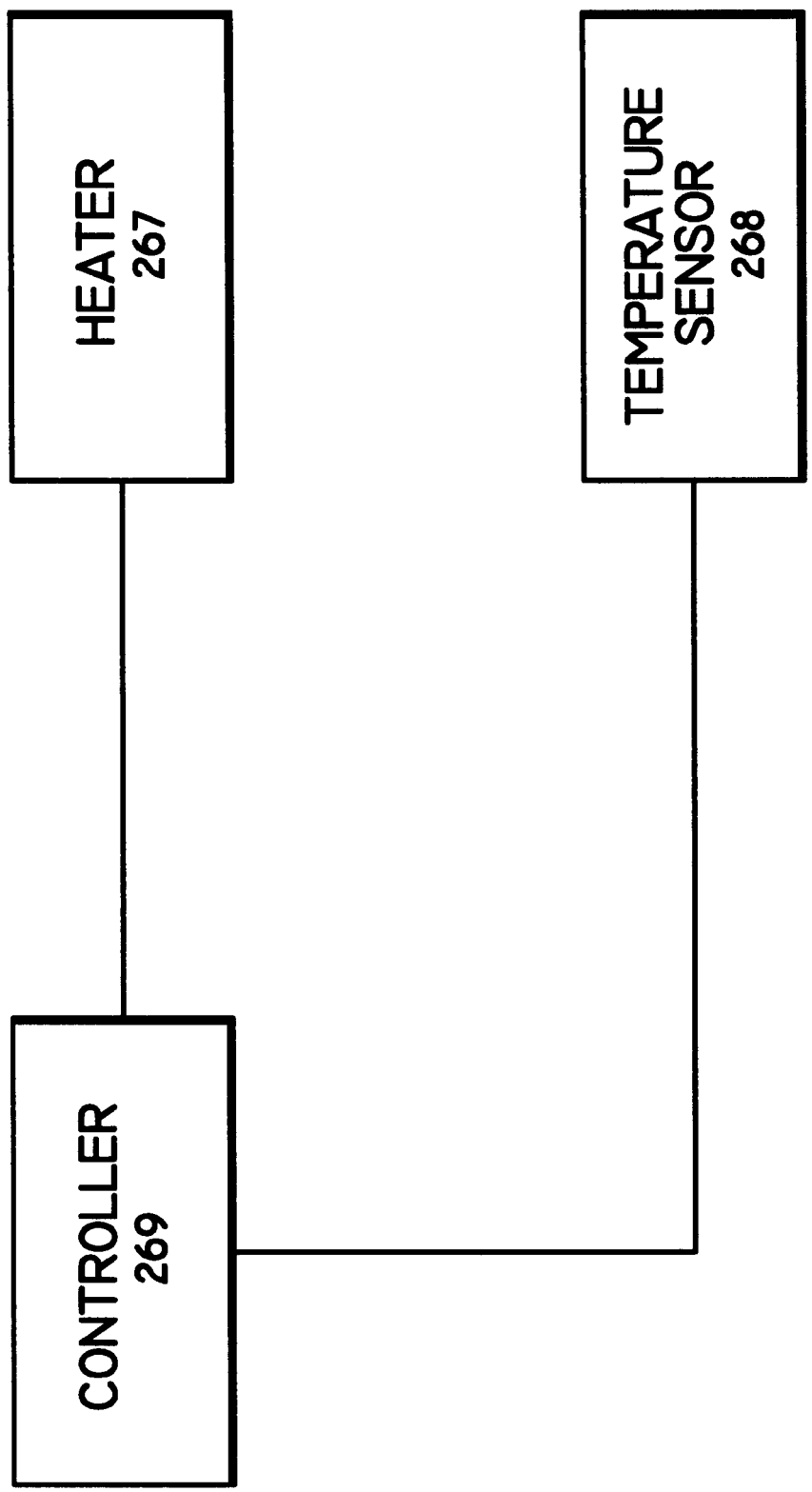
FIG. 10 is a block diagram showing control of temperature of a phantom of the present invention.

Referring to FIG. 10, the phantoms 260, 270 and 280 which are used for calibration or quality assurance according to the present invention are preferably also provided with respective heaters 267, temperature sensors 268 and controllers 269. The temperature sensor 268 are also buried inside the respective phantoms and supply readings of the respective temperatures of the respective phantoms. The controllers 269 monitor the respective temperature readings of the respective temperature sensors 268 and controls the respective heaters accordingly to maintain a predetermined value. For example, the temperature of the phantom can be maintained at approximately body temperature to simulate the measurement of the heel. The temperature at which an ultrasound measurement of the signal passing through one of the phantoms thereby can be controlled.

Coupling gel can be used with the phantoms of the present invention. The coupling gel applied between the phantom and coupling pads does not affect the efficacy of the phantoms. While the typical commercially available water-based coupling gel can be used, a non-aqueous jelly is preferred. For example, petroleum jelly can be used as a coupling gel.

The present invention has been described by using three separate phantoms. However, the relevant features of the respective phantoms can be combined into a single phantom. For example, the single phantom can have the configuration of one of the above-described phantoms, and includes combined materials to provide the above-described properties of the three phantoms so that a received signal that passed through the single phantom has signal characteristics corresponding to these properties.

Having described the preferred phantoms of the present invention with reference to the accompanying drawings, it is to be understood that the invention is not limited to that precise embodiment and that various changes and modifications thereof could be effected by one skilled in the art without departing from the spirit or scope of the novel concepts of the invention, as defined in the appended claims.

What is claimed is:

1. A method of calibrating an ultrasound bone analysis apparatus having a plurality of transducer assemblies with a respective plurality of transducers and a respective plurality of coupling pads and measuring a SOS of a body part, comprising:

providing a plurality of coupling pads having a SOS substantially similar to the SOS of the body part to be analyzed;

adjusting the plurality of transducer assemblies until the plurality of coupling pads are mutually in contact;

transmitting an ultrasound signal through one of the plurality of transducers;

receiving a signal corresponding to the transmitted signal through another one of the plurality of transducers;

determining a first propagation time of the transmitted signal and a first position of the transmitting and receiving transducers;

positioning a body part between the plurality of coupling pads;

transmitting an ultrasound signal through the transmitting transducer;

receiving a signal corresponding to the transmitted signal through the receiving transducer;

determining a second propagation time of the transmitted signal and a second position of the transmitting and receiving transducers; and determining a time for the ultrasound signal to pass from the transmitting transducer to the receiving transducer based on the first and second propagation times and a width of the body part based on the first and second positions.

2. A method of calibrating an ultrasound bone analysis apparatus and measuring a SOS of a body part, comprising:

providing a pair of ultrasound transducer assemblies each having a transducer and a coupling pad, the transducer assemblies being movable between a first position where a face of each coupling pad are in contact and a second position where the face of each coupling pad are coupled to a body part, the plurality of coupling pads having a SOS substantially similar to the SOS of the body part to be analyzed;

transmitting an ultrasound signal from one transducer and receiving a signal corresponding to the transmitted ultrasound signal through the other transducer when the transducer assemblies are in the first position and the second position;

determining a time for the ultrasound signal to pass through the body part;

determining a width of the body part based on positions of the transducers; and calculating a speed of sound of the ultrasound signal passing through the body part using the time for the ultrasound signal to pass through the body part and the width of the body part such that the calculation of the speed of sound includes compensation for squish of the pads.

3. A method of calibrating an ultrasound bone analysis apparatus having at least a pair of transducer assemblies, each transducer assembly having a transducer and a coupling pad and measuring a SOS of a body part, comprising the steps of:

providing a plurality of coupling pads having a SOS substantially similar to the SOS of the body part to be analyzed;

selectively transmitting an ultrasound signal from at least one of the transducers and receiving a signal corresponding to the transmitted ultrasound signal through at least one of the transducers when a face of each pad are in mutual contact and when a body part is positioned between the coupling pads;

determining a time for the ultrasound signal to pass from the at least one transmitting transducer to the at least one receiving transducer when the ultrasound signal is selectively transmitted;

determining a time for the ultrasound signal to pass through the body part using the times for the ultrasound signal to pass from the at least one transmitting transducer to the at least one receiving transducer;

determining a position of each transducer when the ultrasound signal is selectively transmitted;

determining a width of the body part using the positions of the transducers; and calculating a speed of sound of the ultrasound signal passing through the body part using the time for the ultrasound signal to pass through the body part and the width of the body part such that the calculation of the speed of sound includes compensation for squish of the pads.

4. A method of calibrating an ultrasound bone analysis apparatus having a plurality of transducer assemblies, each transducer assembly having a transducer and a coupling pad and measuring a SOS of a body part, comprising the steps of:

providing a plurality of coupling pads having a SOS substantially similar to the SOS of the body part to be analyzed;

adjusting the transducer pads until a face of each pad are mutually in contact;

transmitting an ultrasound signal from one transducer and receiving a signal corresponding to the transmitted ultrasound signal through at least one of the plurality of transducers;

determining a first time associated with passage of the ultrasound signal from the transmitting transducer to the at least one receiving transducer and determining a first position of each transducer;

positioning a body part between the pads and pressing the face of each pad against the body part;

transmitting an ultrasound signal from the transmitting transducer and receiving a signal corresponding to the transmitted ultrasound signal through the at least one receiving transducer;

determining a second time associated with passage of the ultrasound signal through the transducers and the body part and determining a second position of each transducer;

determining a time for the ultrasound signal to pass through the body part using the first and second times;

determining a width of the body part using the first and second positions of the transducers; and calculating a speed of sound of the ultrasound signal passing through the body part using the time for the ultrasound signal to pass through the body part and the width of the body part such that the calculation of the speed of sound includes compensation for squish of the pads.

* * * * *

UNITED STATES PATENT AND TRADEMARK OFFICE
CERTIFICATE OF CORRECTION

PATENT NO.   : 5,935,073
DATED        : August 10, 1999
INVENTOR(S)  : Wilson et al.

It is certified that error appears in the above-identified patent and that said Letter Patent is hereby corrected as shown below:

Cover page, item [63], line 2, please change "5,775,228" to --5,755,228--.

Signed and Sealed this

Fourth Day of January, 2000

Attest:

Attesting Officer

*Acting Commissioner of Patents and Trademarks*